(12) United States Patent  
Dahners

(10) Patent No.: US 8,763,499 B2
(45) Date of Patent: Jul. 1, 2014

(54) SCREW HOLDER-DRIVER APPARATUSES, SYSTEMS AND METHODS

(71) Applicant: The University of North Carolina at Chapel Hill, Chapel Hill, NC (US)

(72) Inventor: Laurence E. Dahners, Chapell Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/689,265

(22) Filed: Nov. 29, 2012

(65) Prior Publication Data

US 2013/0125714 A1     May 23, 2013

Related U.S. Application Data

(63) Continuation of application No. PCT/US2011/039103, filed on Jun. 3, 2011.

(60) Provisional application No. 61/351,695, filed on Jun. 4, 2010.

(51) Int. Cl.
*B25B 15/00*     (2006.01)
*B25B 23/10*     (2006.01)
*F16B 23/00*     (2006.01)

(52) U.S. Cl.
USPC ............................................. 81/451; 411/408

(58) Field of Classification Search
USPC ........ 81/451, 459, 438; 606/60; 411/404, 408
See application file for complete search history.

(56) References Cited

U.S. PATENT DOCUMENTS

| | | | |
|---|---|---|---|
| 355,392 A | 1/1887 | Fellers | |
| 601,188 A | 3/1898 | Webster | |
| 881,296 A | 3/1908 | Briddon | |
| 1,229,793 A | 6/1917 | Ryan | |
| 1,889,330 A | 11/1932 | Humes | |
| 1,925,385 A | 9/1933 | Humes | |
| 2,028,546 A | 1/1936 | Frank | |
| 2,312,869 A * | 3/1943 | Boyer | 81/438 |
| 2,566,673 A | 9/1951 | Nygaard | |
| 2,579,438 A | 12/1951 | Longfellow | |
| 2,604,912 A * | 7/1952 | Walker | 81/451 |
| 2,633,168 A | 3/1953 | Mahaffey | |
| 2,762,408 A | 9/1956 | Baldwin | |

(Continued)

OTHER PUBLICATIONS

International Search Report and Written Opinion for WO2011/153455 dated Feb. 9, 2012.

*Primary Examiner* — David B Thomas
(74) *Attorney, Agent, or Firm* — Jenkins, Wilson, Taylor & Hunt, P.A.

(57) ABSTRACT

Screw driver-holder apparatuses, systems and methods are provided and can include a screw and a screwdriver. The screw can include a threaded screw body and a screw head, and the screw head can include a socket and a screw head surface surrounding the socket. The screwdriver can include a hollow sleeve with a longitudinal bore and a first end defining a screw engagement surface and a driving shaft positioned within the longitudinal bore of the hollow sleeve and rotatable relative to the hollow sleeve. The driving shaft can further include a first end extending beyond the first end of the hollow sleeve, a second end opposite the first end, and a stop restricting axial movement of the sleeve towards the second end of the driving shaft. The first end can include a protruding tip adapted for engaging the socket of the screw head.

23 Claims, 5 Drawing Sheets

(56) References Cited

U.S. PATENT DOCUMENTS

| | | | | |
|---|---|---|---|---|
| 2,952,285 A | | 9/1960 | Roosli | |
| 2,954,809 A | | 10/1960 | Loewy | |
| 3,392,767 A | * | 7/1968 | Stillwagon, Jr. | 81/451 |
| 3,449,988 A | * | 6/1969 | Gallo, Sr. | 81/176.15 |
| 3,489,041 A | * | 1/1970 | Hauenstein et al. | 81/176.15 |
| 3,579,677 A | * | 5/1971 | Ullman | 7/100 |
| 3,604,487 A | | 9/1971 | Gilbert | |
| 3,901,298 A | | 8/1975 | Eby | |
| 4,140,161 A | | 2/1979 | Russo | |
| 4,195,772 A | | 4/1980 | Nishimura | |
| 4,363,250 A | | 12/1982 | Suga | |
| 4,581,962 A | | 4/1986 | Marbourg | |
| 4,736,658 A | | 4/1988 | Jore | |
| 4,763,548 A | | 8/1988 | Leibinger | |
| 4,936,172 A | | 6/1990 | Jackson | |
| 5,056,387 A | * | 10/1991 | Cook | 81/456 |
| 5,207,122 A | | 5/1993 | Minagawa | |
| 5,341,708 A | | 8/1994 | Nick | |
| 5,438,895 A | | 8/1995 | Bassell | |
| 5,492,039 A | | 2/1996 | Haikal | |
| 5,509,330 A | | 4/1996 | Nick | |
| 5,562,547 A | | 10/1996 | Borzone | |
| 5,605,080 A | | 2/1997 | Pfefferle | |
| 5,791,212 A | * | 8/1998 | Han | 81/453 |
| 6,082,833 A | | 7/2000 | Hosoya | |
| 6,112,623 A | | 9/2000 | Bigand | |
| 6,148,699 A | | 11/2000 | Han | |
| 6,155,145 A | | 12/2000 | Oh et al. | |
| 6,244,141 B1 | | 6/2001 | Han | |
| 6,286,401 B1 | | 9/2001 | Hajianpour | |
| 6,436,100 B1 | | 8/2002 | Berger | |
| 6,497,166 B1 | | 12/2002 | Fleckenstein | |
| 6,543,317 B1 | | 4/2003 | Rinner | |
| 6,565,573 B1 | | 5/2003 | Ferrante | |
| 6,620,167 B2 | | 9/2003 | Deslauriers et al. | |
| 6,857,343 B1 | | 2/2005 | Easterbrooks | |
| 7,073,415 B2 | * | 7/2006 | Casutt et al. | 81/451 |
| 7,096,768 B1 | * | 8/2006 | Chen | 81/438 |
| 7,107,882 B1 | * | 9/2006 | Chang | 81/451 |
| 7,174,812 B1 | | 2/2007 | Chiang | |
| 7,246,540 B2 | | 7/2007 | Rillera | |
| 7,325,470 B2 | | 2/2008 | Kay | |
| 8,459,155 B2 | * | 6/2013 | Canizares et al. | 81/451 |
| 2003/0023246 A1 | * | 1/2003 | Gotfried | 606/104 |
| 2005/0098002 A1 | | 5/2005 | Holland-Letz | |
| 2007/0010816 A1 | | 1/2007 | Wilkinson | |
| 2008/0045970 A1 | * | 2/2008 | Saidha et al. | 606/104 |
| 2008/0243133 A1 | | 10/2008 | Heinz | |
| 2009/0326545 A1 | | 12/2009 | Schaffhausen | |
| 2010/0094343 A1 | * | 4/2010 | Pham et al. | 606/246 |
| 2012/0017728 A1 | * | 1/2012 | Schmidt | 81/57.37 |
| 2012/0057949 A1 | * | 3/2012 | Canizares et al. | 411/410 |

* cited by examiner

SCREW HOLDER-DRIVER APPARATUSES, SYSTEMS AND METHODS

CROSS REFERENCE TO RELATED APPLICATIONS

This application is a continuation of and claims priority to PCT/US2011/039103 filed Jun. 3, 2011 which claims the benefit of and priority to U.S. Provisional Patent Application Ser. No. 61/351,695, filed Jun. 4, 2010, the entire disclosures of which are herein incorporated by reference.

TECHNICAL FIELD

The subject matter disclosed herein relates generally to screw holders and screwdrivers. More particularly, the subject matter disclosed herein relates to apparatuses, systems and methods for securely and releasably holding a screw on a screwdriver.

BACKGROUND

In many situations it is desirable that a screw be securely attached to a screwdriver. Such an arrangement enables the operator to place the screw into the screw hole with one hand because it is not necessary to use a hand to hold the screw on the driver. Further, when firmly attached, "buckling" of the screw-screwdriver assembly can be prevented if the operator accidentally tries to drive the screw slightly off-angle. In addition, in some situations when trying to place a screw down into a small hole, there sometimes is not room for the operator's finger to hold the screw on the end of the screwdriver. For example, in the case of surgical screws, once the screw and driver are turned downward into the surgical wound, if the screw falls off the driver, it can be lost in the wound. Further in regard to surgical screws, when working under poor visualization due to a limited dissection and other causes of poor exposure (e.g., minimally invasive surgery), if the screw misses the predrilled hole and slips off the bone, it can plunge into the surrounding muscle. Likewise, when the screwdriver is pulled back it leaves the screw in the surrounding tissue if the screw is not firmly attached to the driver. Retrieving such a lost screw can be extremely problematic.

Although many attempts have been made to provide secure attachment of screws to their drivers, almost all of these devices function by providing "fingers" disposed around the screwhead that grasp the screw and hold it on the driver. Some such devices are stoutly designed and might function to hold the screw securely, but they do so at the cost of being large and bulky, which is especially undesirable in minimally invasive surgery. In addition, such devices are frequently exceedingly complex and would not tolerate surgical autoclaving. Also, such fingers tend to become caught under the head of the screw when it is fully inserted. When the fingers catch under the head of the screw in this way, the screw must be loosened to remove the fingers and then retightened. Thus, although such devices are currently in use in orthopedic surgery, they have significant limitations.

Alternatively, some devices function by having a hexagonal tip screwdriver in which the tip expands within the head of the screw thus gripping the hex socket in the screw from the inside. This kind of fixation is not very secure, however, and such devices are known to drop screws in use. They can also require multiple hands to assemble the screw to the screwdriver (e.g., one holds the screw, another holds the driver, a third tightens the ring that expands the tip of the screwdriver).

Some devices are designed to be used with special screws that have internal threads on the heads of the screws. Thus, compared to the hexagonal tip devices, these systems can provide more secure fixation, but they can still have the disadvantage of requiring that the operator tighten the screw onto the driver (e.g., a three hand operation), then assemble the driver onto the power driving tool before using it. Then, after insertion of the screw, the power tool must be removed from the driver to allow the bolt that holds the screw on the driver to be removed, and this removal step can often require the use of even another tool to loosen the bolt.

Accordingly, although a variety of different screwdriver designs have been used to address the problem of screw-screwdriver fixation, each of these designs has significant flaws. As a result, it would be desirable for apparatuses and methods to be developed for securely yet releasably holding a screw on a screwdriver.

SUMMARY

In accordance with this disclosure, apparatuses, systems and methods for securely and releasably holding a screw on a screwdriver are provided. In one aspect, a screwdriver assembly is provided. The screwdriver assembly can comprise a hollow sleeve comprising a longitudinal bore and a first end defining a screw engagement surface and a driving shaft positioned within the longitudinal bore of the hollow sleeve and rotatable relative to the hollow sleeve. In addition, the driving shaft can comprise a first end extending beyond the first end of the hollow sleeve, a second end opposite the first end, and a stop restricting axial movement of the sleeve towards the second end of the driving shaft. The first end can comprise a protruding tip adapted for engaging a corresponding socket in a head of a screw.

In another aspect, a method for driving a screw is provided. The method can comprise positioning a driving shaft within a longitudinal bore of a hollow sleeve, the driving shaft rotatable relative to the hollow sleeve, and connecting a screw to the driving shaft by engaging a protruding tip of the driving shaft with a corresponding socket in a head of the screw. When the protruding tip is at least partially engaged with the socket of the screw, a first end of the hollow sleeve can contact the head of the screw. The method can further comprise rotating one or both of the driving shaft or the hollow sleeve in a first direction to advance the screw, and rotating the driving shaft in a second direction opposite the first direction to disengage the protruding tip from the socket of the screw.

In yet another aspect, the present subject matter provides a fixation system comprising a screw and a screwdriver. The screw can comprise a threaded screw body and a screw head, the screw head comprising a socket and a screw head surface surrounding the socket. The screwdriver can comprise a hollow sleeve comprising a longitudinal bore and a first end defining a screw engagement surface and a driving shaft positioned within the longitudinal bore of the hollow sleeve and rotatable relative to the hollow sleeve. The driving shaft can further comprise a first end extending beyond the first end of the hollow sleeve, the first end comprising a protruding tip adapted for engaging the socket of the screw head, a second end opposite the first end, and a stop restricting axial movement of the sleeve towards the second end of the driving shaft.

In still another aspect, the present subject matter provides a screw comprising a threaded screw body adapted for engagement of a material such as wood or bone and a screw head. The screw head can comprise an internally-threaded socket adapted for engaging an externally-threaded driving shaft of a screwdriver.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which.

DETAILED DESCRIPTION

The present subject matter provides apparatuses, systems, and methods for securely yet releasably holding a screw on a screwdriver. Specifically, a driver, which can be normally be attached to a power driving tool, can have a threaded tip which can mate with a threaded socket in the head of a screw. An operator can simply hold the screw to the end of the driver and rotate the driver (e.g., by operating a connected power driving tool briefly in the forward direction) to attach the screw to the driver. The operator can place the tip of the screw in position on the target workpiece (e.g., a bone, a plate) and again use the driver to insert the screw (e.g., by again operating the driving tool in the forward direction). Once the screw is inserted, the operator can use the driver (e.g., by operating the driving tool briefly in the reverse direction) to cause the driver to drop off the screw, allowing the operator to move on to the next screw insertion procedure.

Figure 1A:
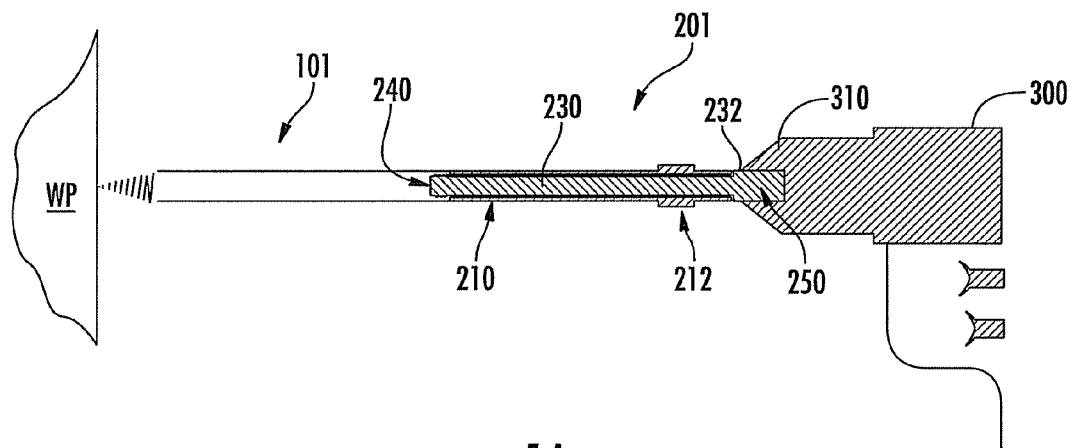
FIGS. 1A and 1B are side cutaway views of a screw holder and screwdriver assembly in two different operating states according to an embodiment of the presently disclosed subject matter.
Figure 1B:
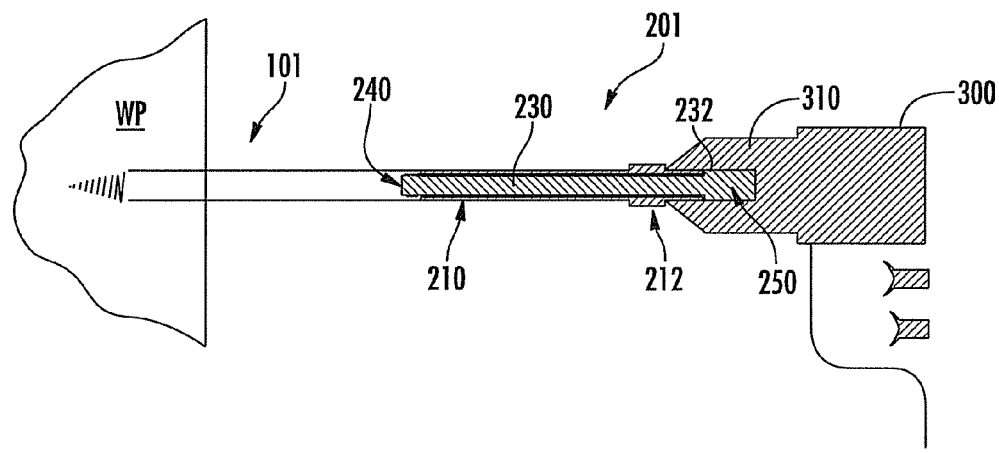

For example, in one aspect, the present subject matter provides apparatuses, systems, and methods for holding and driving a pin or screw, generally designated 101, using a first screwdriver assembly, generally designated 201. As shown in FIGS. 1A and 1B, first screwdriver assembly 201 can comprise a hollow sleeve generally designated 210 defining a longitudinal bore there through and a driving shaft 230 positioned within the longitudinal bore of sleeve 210 and longitudinally movable and rotatable relative to sleeve 210. Driving shaft 230 can comprise a first end 240 adapted for engaging a corresponding socket in a head of pin 101. For example, first end 240 can be adapted to be inserted into and secured to an end of pin 101. Specifically, first end 240 can comprise a threaded tip that can engage a correspondingly threaded internal bore of pin 101. Driving shaft 230 can further comprise a second end 250 opposite first end 240, and a stop 232 restricting axial movement of sleeve 210 towards second end 250 of driving shaft 230.

To drive pin 101 using first screwdriver assembly 201, a driving tool 300 (e.g., a power drill) can be connected to second end 250 of driving shaft 230, such as by gripping second end 250 with a chuck 310 as shown in FIG. 1A. First end 240 of driving shaft 230 can engage pin 101 (e.g., first end 240 can engage a threaded socket in pin 101), and sleeve 210 can slide over driving shaft 230 towards pin 101. Because stop 232 only allows driving shaft 230 to extend a predetermined distance through sleeve 210, a point can be reached at which driving shaft 230 cannot be advanced further into the end of pin 101, and so further advancement of driving shaft 230 causes pin 101 to be turned and thus advanced. Accordingly, in this state, rotation of driving shaft 230 can thus drive pin 101 into a work piece WP (e.g., a bone, a plate).

When pin 101 is driven to a desired depth, reversing the above procedure can disengage driving shaft 230 from the end of pin 101. In particular, where first end 240 comprises a threaded tip, reversing the driving direction of driving tool 300 can unscrew driving shaft 230 from the end of pin 101 and thus disengage first screwdriver assembly 201 from pin 101. In situations where the friction between sleeve 210 and driving shaft 230 (e.g., friction of contact at stop 232) is greater than the friction between pin 101 and work piece WP, sleeve 210 can be braced against rotation to prevent movement of sleeve 210 as driving shaft 230 is rotated. In this regard, sleeve 210 can comprise a grippable portion 212, such as a portion having a hexagonal cross-section that can be securely grasped by a wrench, which can be engaged by a wrench or similar tool to hold sleeve 210 in place while driving shaft 230 is rotated. In this way, driving shaft 230 can be rotated in a reverse direction relative to sleeve 210 to disengage from pin 101.

If the user desires to unscrew pin 101 instead of disengaging first screwdriver assembly 201 from pin 101, the operator can connect driving tool 300 to sleeve 210 rather than to driving shaft 230, such as by gripping sleeve 210 with chuck 310 as shown in FIG. 1B. Because when driving shaft 230 is engaged with the end of pin 101, sleeve 210 is effectively locked between the end of pin 101 and stop 232, sleeve 210 can exert a force on pin 101. Accordingly, by rotating sleeve 210 in reverse, pin 101 can likewise be rotated in a reverse direction to remove it from work piece WP, whereas similar reverse rotation of driving shaft 230 would only cause driving shaft 230 to disengage from pin 101 as discussed herein above.

Figure 2A:
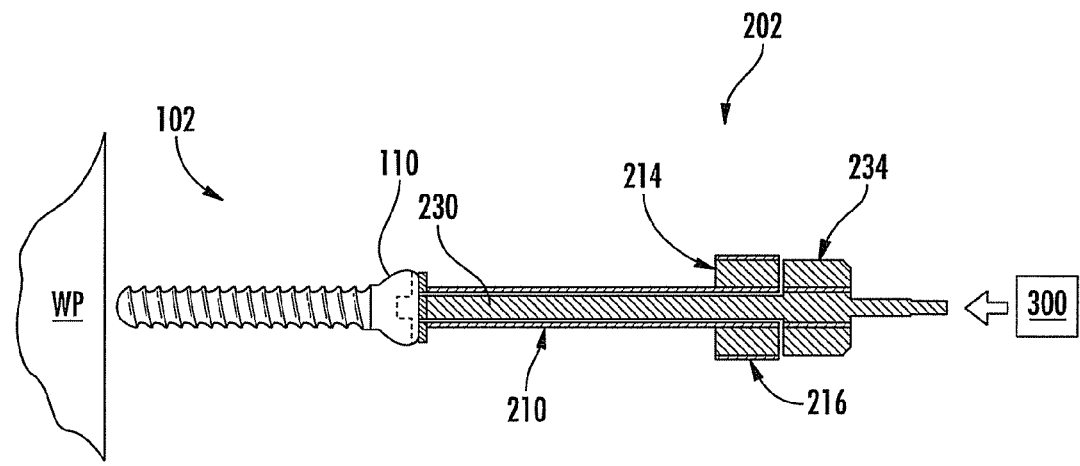
FIGS. 2A and 2B are side cutaway views of a screw holder and screwdriver assembly in two different operating states according to an embodiment of the presently disclosed subject matter.
Figure 2B:
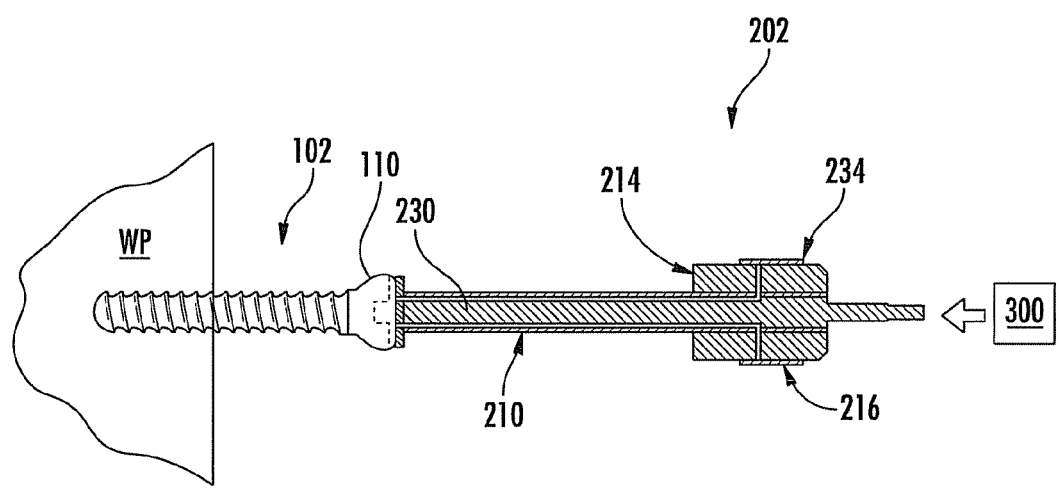

In another aspect, the present subject matter provides an alternative configuration for a second screwdriver assembly, generally designated 202, shown in FIGS. 2A and 2B. Similar to the configuration described above with reference to first screwdriver assembly 201, second screwdriver assembly 202 can comprise a driving shaft 230 that can be adapted for engaging a corresponding socket in a head of a screw, generally designated 102, which can have an integral head 110. Specifically, for example, driving shaft 230 can be screwed into a central threaded hole in head 110 of screw 102. A sleeve 210 positioned about driving shaft 230 can prevent driving shaft 230 from "bottoming" in the socket and binding. Once inserted and at least slightly tight, the operator can insert screw 102 into a work piece WP (e.g., a bone) by rotating driving shaft 230.

Contrary to the first configuration, however, driving shaft 230 according to the subject matter of this aspect can comprise a shaft handle 234 that can serve multiple functions. First, shaft handle 234 can act as a stop for restricting axial movement of sleeve 210 towards second end 250 of driving shaft 230 (i.e., similar to stop 232). In addition, shaft handle 234 can act as a hand grip for manual rotation of driving shaft 230. Similarly, sleeve 210 can comprise a sleeve handle 214, which can act as a hand grip for manual rotation of sleeve 210. A slide lock 216 can be moved to engage sleeve handle 214 to shaft handle 234 for rotation of sleeve 210 and driving shaft 230 together. For example, slide lock 216 can have internal grooves to span the gap between the handles to rotationally lock sleeve 210 and driving shaft 230 together.

In this arrangement, driving shaft 230 can be engaged with an end of screw 102 in a manner similar to the procedure discussed above. Once engaged, screw 102 can be driven by rotating shaft handle 234 in a driving direction. Alternatively, a power driving tool 300 can be coupled to an end of driving shaft 230 rather than requiring manual operation of the assembly. Once screw 102 is driven to a desired depth in workpiece WP, the procedure can be reversed to disengaged shaft 230 from screw 102. Again, if the friction between sleeve 210 and driving shaft 230 (e.g., friction of contact at shaft handle 234) is greater than the friction between screw 102 and workpiece WP, sleeve handle 214 can be held in place to prevent rotation of sleeve 210 while shaft handle 234 is rotated in reverse to disengage driver 202 from screw 102 without causing screw 102 to back out.

Conversely, if it is desired to remove screw 102 from work piece WP, sleeve handle 214 can be purposely rotated in a reverse direction. In addition, slide lock 216 can be moved to engage sleeve handle 214 to shaft handle 234, and rotation of driving shaft 230 in a reverse direction (e.g., through operation of driving tool 300) can cause reverse rotation of sleeve 210 to thereby remove screw 102 from work piece WP.

In either configuration, the operator can choose to leave first or second screwdriver assembly 201 or 202 connected to driving tool 300. In this regard, with respect to second screwdriver assembly for example, connecting screw 102 to second screwdriver assembly 202 can comprise holding screw 102 up to first end 240 of driving shaft 230 and operating driving tool 300 in a forward direction to attach driving shaft 230 to screw 102. Screw 102 can then be placed against workpiece WP and driven into place. Reversing the direction of driving tool 300 can disengage driving shaft 230 from screw 102, allowing the operation to be repeated. To disengage a screw 102 that is solidly locked-on to driving shaft 230, sleeve 210 can be held in place (e.g., by sleeve handle 214) while driving tool 300 is operated in reverse. If the operator wishes to back out or remove screw 102, with sleeve 210 solidly locked together to driving shaft 230, such as by "sandwiching" sleeve 210 between screw 102 and a portion of driving shaft 230 (e.g., shaft handle 234) and/or by engaging slide lock 216, driving tool 300 can be operated in reverse to back screw 102 out of work piece WP.

Regarding the features of pin 101 and screw 102 and of first and second screwdriver assemblies 201 and 202 that allow the components to be coupled together, a number of exemplary designs are shown in FIGS. 3 through 6B. It should be noted that FIGS. 3 through 6B illustrate various configurations for screw 102 having an integral head 110 and second screwdriver assembly 202, but the principles discussed herein below with reference to these configurations can be equally applied to configurations of pin 101 and/or first screwdriver assembly 201. In a first configuration shown in FIG. 3, for example, a first screw 102a can comprise a head 110 and a threaded body 120. Head 110 can include one or more features intended to assist engagement of a screwdriver assembly, including but not limited to a threaded socket 112, a textured head surface 114 (e.g., a serrated surface), and/or one or more slots 116. Second screwdriver assembly 202 can be complementarily designed to interact with one or more of these engagement features. For example, a first screwdriver assembly arrangement, which is designated 202a in FIG. 4A, can be configured such that first end 240 of driving shaft 230 comprises a protruding tip 242 having a threaded outer surface 244. Tip 242 can be sized and threaded outer surface 244 can be profiled to be complementary to the size and profile of threaded socket 112 of first screw 102a. For example, tip 242 can extend beyond first end 220 of sleeve 210 by a distance d that can be less than a depth of corresponding threaded socket 112 on first screw 102a. In this configuration, engagement of first screw 102a can involve aligning tip 242 with threaded socket 112 and rotating driving shaft 230 such that threaded socket 112 enmeshes with threaded outer surface 244, but tip 242 will be prevented from "bottoming" in threaded socket 112 and binding.

Those having ordinary skill in the art should recognize that threaded socket 112 of first screw 102a (and similarly threaded outer surface 244 of driving shaft 230) can be threaded in either a right-hand (i.e., clockwise tightening) or left-hand (i.e., counterclockwise tightening) direction depending on the preference of the operator or considerations of the intended use. For example, if threaded socket 112 is designed to be right-hand threaded, operation of screwdriver assembly can be accomplished as described above, with both engagement of driving shaft 230 to first screw 102a and driving of first screw 102a being accomplished by rotating driving shaft 230 in the same direction (i.e., clockwise). In this orientation, backing first screw 102a out of the work piece can be accomplished by rotating sleeve 210 in a counterclockwise direction.

Conversely, if threaded socket 112 is threaded in a left-hand direction, engagement of driving shaft 230 to first screw 102a can be accomplished by rotating driving shaft 230 counterclockwise, but driving of first screw 102a can accomplished by rotating sleeve 210 in a clockwise direction. In this configuration, first screw 102a can be backed out of the work piece by rotating driving shaft 230 in a counterclockwise direction. In this way, since this direction is the same as the direction that can be used to tighten the connection between driving shaft 230 to first screw 102a, more torque can be applied for the removal of first screw 102a without risking disengagement of first screw 102a from driving shaft 230. In other words, when driving shaft 230 "bottoms" in threaded socket 112, it can begin to extract first screw 102a. Such a feature can be especially desirable in orthopedic surgery applications where removal of screws from a patient after the bone is healed can be difficult. In addition, if the threads of first screw 102a within the bone are stripped (which is often the case), second screwdriver assembly 202 having first arrangement 202a can still extract first screw 102a by pulling it out, whereas current screwdrivers cannot "pull" a screw out of a hole in which it is stripped (i.e., they can only rotate to unscrew, but they are generally unable to apply tension to pull the screw out).

Alternatively, threaded socket 112 can be threaded in both directions simultaneously (i.e., the threads for both directions are present and cross one another). In this configuration, either a right-hand-threaded version or a left-hand-threaded version of driving shaft 230 can be used with first screw 102a for different operations. Namely, a right-hand-threaded version of driving shaft 230 can be used to drive first screw 102a into a work piece, whereas a left-hand-threaded version can be used to extract first screw 102a from the work piece.

Figures 3, 4A:
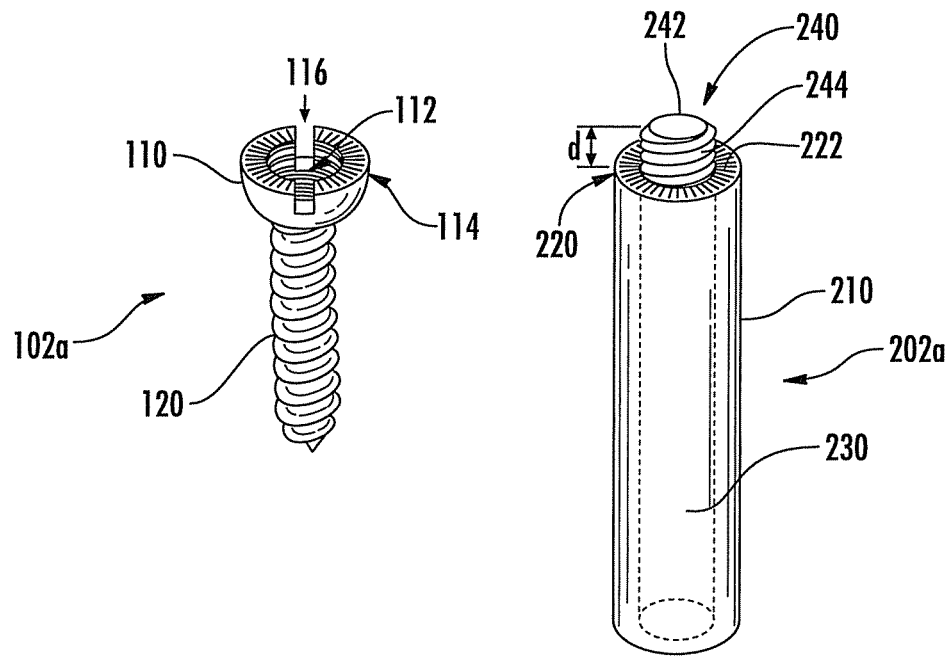
FIG. 3 is a perspective view of a screw for use with a screw holder and screwdriver assembly according to an embodiment of the presently disclosed subject matter.
FIGS. 4A, 4B, and 4C are perspective views of screw holder and screwdriver assemblies for use with the screw shown in FIG. 3.

Regarding additional engagement features, head 110 of first screw 102a can comprise a textured head surface 114 that can enhance frictional coupling of head 110 to sleeve 210 when sleeve 210 is pressed against head 110 (e.g., because of force exerted by stop 232 or shaft handle 234). In addition, as shown in FIG. 4A, sleeve 210 can be similarly profiled to further enhance this interaction. Specifically, for example, sleeve 210 can have a first end 220, which can define a textured sleeve surface 222 (e.g., a serrated surface). Textured sleeve surface 222 can be designed to interact with textured head surface 114 of head 110 of first screw 102a such that when sleeve 210 is pressed against the end of first screw 102a (e.g., against head 110), the textured surfaces can act to increase the frictional force of this contact.

In this configuration, head 110 of first screw 102a and first end 220 of sleeve 210 can fit together positively for rotation together. At least a roughened surface can be present on both for increasing frictional contact forces, but one or both components can be further modified to create a better fit. For example, textured head surface 114 and textured sleeve surface 222 can each comprise radially-arranged serrations that can interdigitate with one another. In this way, engaging driving shaft 230 tightly into socket 112 of first screw 102a can cause such serrations to compress together, and thus turning sleeve 210 in reverse can act to readily back out first screw 102a. The serrations can be sharply edged, or they can be rounded and/or undulating to prevent glove and tissue damage. Further, other configurations (e.g., a "saddle shape" profile for each surface) can likewise be incorporated to provide improved coupling in a similar manner.

Of course, it should be recognized that the surfaces of one or both of head 110 or sleeve 210 can be smooth, and second screwdriver assembly 202 can still operate to drive first screw 102a. With smooth surfaces, however, it can be comparatively more difficult for sleeve 210 to cause rotation of first screw 102a, such as to back first screw 102a out for repositioning. In such situations, the operator may need to switch to a different version of second screwdriver assembly 202 (e.g., left-hand-threaded version discussed above) to extract first screw 102a, which can be considered an undesirable extra step.

Figure 4B:
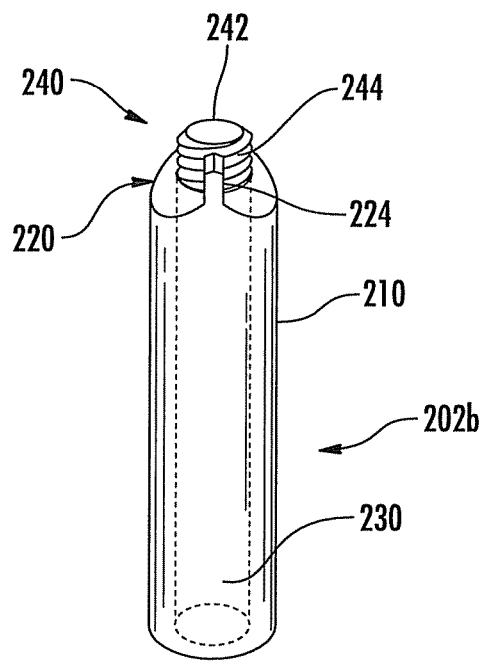

Regarding yet another engagement feature, head 110 of first screw 102a can comprise one or more slots 116 that can be used in a manner similar to the slots in conventional screws. For example, as shown in FIG. 3, head 110 can comprise a single slot 116 positioned across a diameter of head 110. To drive first screw 102a having this configuration, a conventional screwdriver having a flat-bladed configuration can be used. Alternatively, a second screwdriver assembly arrangement, which is designated 202b in FIG. 4B, can be complementarily designed to interact with slots 116. For example, as shown in FIG. 4B, sleeve 210 can comprise one or more blades 224 that are spaced about first end 220 to correspond to the positions of slots 116 in head 110 of first screw 102a. Specifically, to correspond to the single-slot design of first screw 102a shown in FIG. 3, sleeve 210 can comprise two blades 224 positioned opposing each other.

With this configuration, before or during engagement of tip 242 of driving shaft 230 with threaded socket 112 of first screw 102a, blades 224 of sleeve 210 can be aligned with slot 116. In this way, engagement of first screw 102a can involve coupling of both driving shaft 230 and sleeve 210 to head 110 of first screw 102a. As a result, a great degree of control can be exercised on first screw 102a, which can help to obtain extremely secure fixation and easy removal of first screw 102a to and from a work piece or bone. Further, as shown in FIG. 4B, first end 220 of sleeve 210 can have a profile that tapers away from blades 224 to make it easier to insert blades 224 into slot 116 should any tissue be interposed.

Figure 4C:
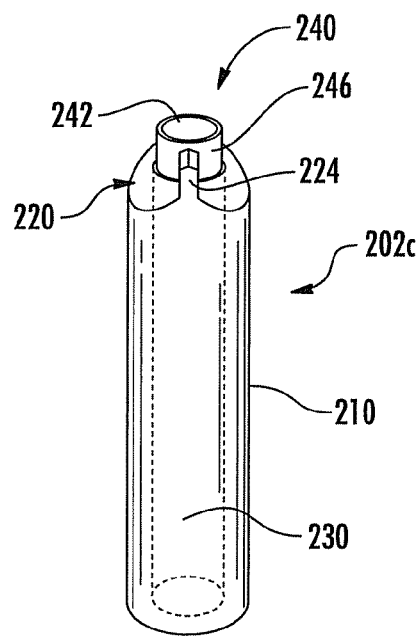

In third screwdriver assembly arrangement, which is designated 202c in FIG. 4C, protruding tip 242 of driving shaft 230 of second screwdriver assembly 202 can comprise an unthreaded and smooth outer surface 246 (i.e., rather than threaded outer surface 244). Using second screwdriver assembly 202 having third arrangement 202c, rather than threading driving shaft 230 onto first screw 102a, smooth outer surface 246 allows driving shaft 230 to slide into threaded socket 112 and serve to "center and align" driving shaft 230 on first screw 102a. Such centering and alignment can be accomplished in comparatively less time than engaging the threaded version of driving shaft 230 to threaded socket 112 and can allow blades 224 to more easily and securely engage slot 116. By comparison, using a traditional flat-blade screwdriver in a similar situation can often involve problems of the screwdriver sliding to one side in the slot, where it can damage the slot by twisting out of it, and/or operation of the driver when not fully aligned, which can tend to damage (i.e., "strip") the head of the screw. Furthermore, driving shaft 230 having a smooth outer surface 246 at tip 242 can snugly slide into the threaded socket 112, which can allow the operator to "direct" the movement of first screw 102a, thus enabling it to be "pointed" toward the hole in the other side of the work piece or bone.

Third arrangement 202c can be used, for example, for tightening screws after initial insertion during bone surgery. It is frequently the case that, after placing all the screws, the later screws occasionally can deform the plate and bone towards one another, leaving the initial screws slightly loose. Thus, the surgeon can sometimes need to go back and hand-tighten all the screws at the end of the procedure. The surgeon may prefer not to go through the steps necessary to thread a driver onto the screw at that point, however, and would instead prefer the quick action of the driving head in FIG. 4C.

Further regarding slots 116 and blades 224, it can be recognized that similar to the many designs for conventional screw-screwdriver configurations that exist, a variety of different configurations for slots 116 and blades 224 can be implemented according to the present subject matter. For example, referring to FIGS. 5A and 5B, a second screw 102b can comprise two slots 116 each extending across head 110 (e.g., perpendicular slots that intersect at a center of head 110). A fourth screwdriver assembly arrangement, which is designated 202d in FIG. 5B, can be configured such that sleeve 210 can comprise four blades 224 spaced about first end 220 (e.g., equally distributed at 90 degree intervals). In this configuration, the system can operate in a manner similar to any of a variety of cruciform-type screwdriver configurations.

Figure 5A:
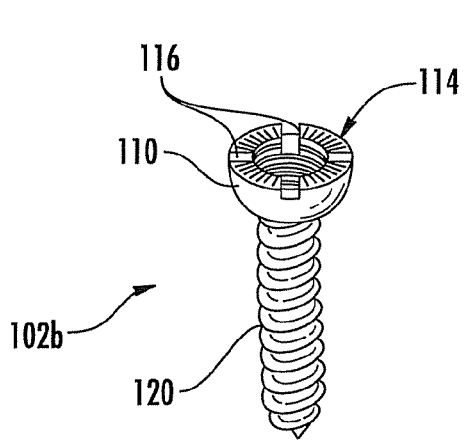
FIG. 5A is a perspective view of a screw for use with a screw holder and screwdriver assembly according to an embodiment of the presently disclosed subject matter.
Figure 5B:
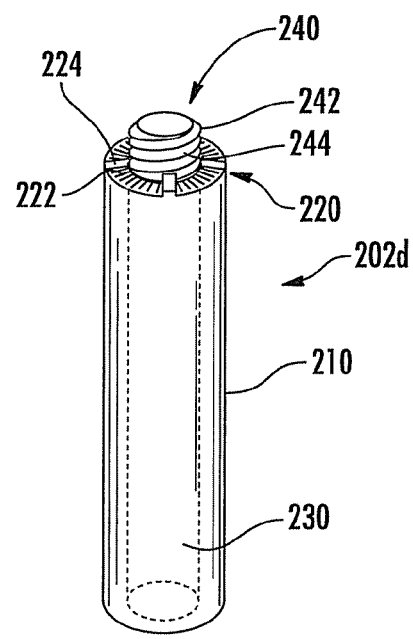
FIG. 5B is a perspective view of a screw holder and screwdriver assembly for use with the screw shown in FIG. 5A.

Furthermore, fourth arrangement 202d shown in FIG. 5B provides examples of a number of additional modifications to the system that can be implemented. For example, the features of a textured engagement surface and slot-engaging blades can be implemented together. As shown in FIG. 5B, first end 220 of sleeve 210 can comprise a plurality of blades 224 spaced apart from each other, and textured sleeve surface 222 can be provided on surfaces of first end 220 between blades 224.

In addition, blades 224 can be formed with a non-uniform profile. Specifically, blades 224 can be tapered outward toward their outer edges, and second screw 102b can be complementarily profiled such that slots 116 taper inwardly so that slots 116 each leave a constant amount of material at the lateral surface of the head 110. One benefit of such a head design can be that whereas a complete slot can significantly weaken the screwhead such that the two "halves" of the screwhead (i.e., portions on either side of a given slot) might "split" apart if a blade screwdriver was turned against heavy resistance, a tapered slot can provide greater resistance against this kind of failure. Taking this principle a step further, maintaining a relatively thin "wall" around the perimeter of head 110 (not shown) can further strengthen head 110 against such phenomena and help with centering and alignment control over second screw 102b. In addition, slot 116 can be made deeper without excessively weakening head 110. Finally, such a configuration can help in manufacturing where tapping threads into a "blind hole" is difficult because there is no place for the swarf to go. A deep slot, cut before tapping the threads, would provide a relief zone for the swarf.

Figures 6A, 6B:
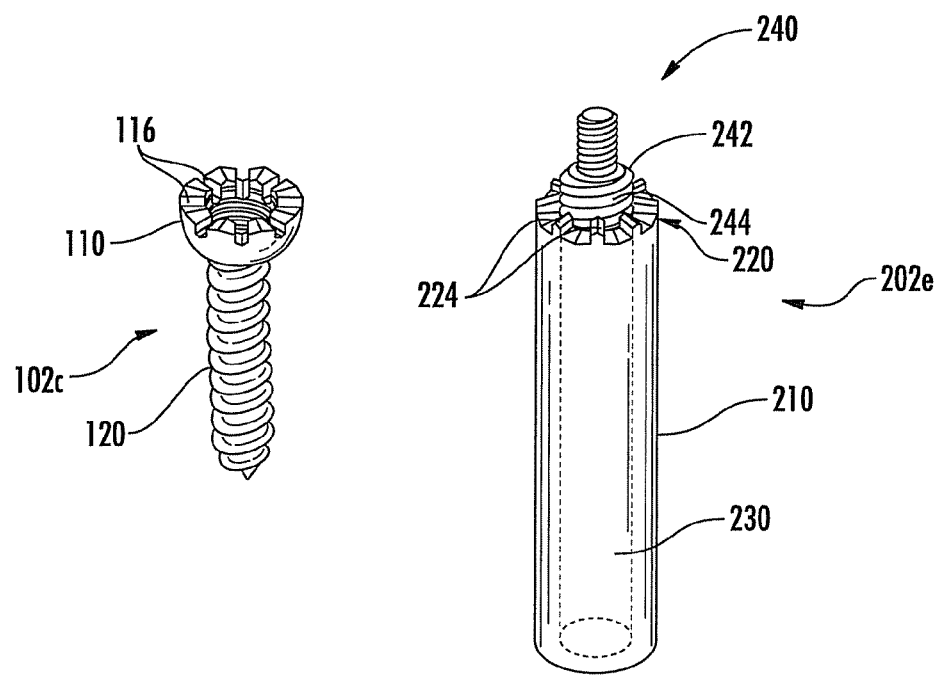
FIG. 6A is a perspective view of a screw for use with a screw holder and screwdriver assembly according to an embodiment of the presently disclosed subject matter.
FIG. 6B is a perspective view of a screw holder and screwdriver assembly for use with the screw shown in FIG. 6A.

In yet a further alternative configuration, FIG. 6A shows that a third screw 102c can comprise a plurality of slots 116 arranged in a "double cruciform" pattern. In a fifth screwdriver assembly arrangement, which is designated 202e in FIG. 6B, sleeve 210 can correspondingly comprise eight blades 224 spaced about first end 220 of sleeve 210. One advantage of these designs can be that the ridges between slots 116 can direct blades 224 so that they readily fall into engagement therein. Thus, the operator can simply place second screwdriver assembly 202 on head 110 of third screw 102c, spin it forward (e.g., using driving tool 300), and blades 224 can interdigitate with slots 116 nearly as easily as they would grip radial serrations. In this regard, versions of second screwdriver assembly 202 having such multiple-blade configurations (e.g., fifth arrangement 202e) can be used in much the same way as versions having only textured engagement surface (e.g., textured sleeve surface 222 in first arrangement 202a), but the use of blades with slots can achieve a comparatively more positive fit, which can make it easier to unscrew third screw 102c by turning sleeve 210 in reverse.

In surgery, bone screws can often be held in a "caddy." The actual step of picking the screws out of the caddy, however, is often clumsy in surgical gloves. Using screws and screwdriver assemblies according to the subject matter disclosed herein, this difficulty can be addressed since the driver can be placed on the screw head as it rests in the caddy and operated forward to attach the screw and ease the step of removing the screw from the caddy.

Figure 7:
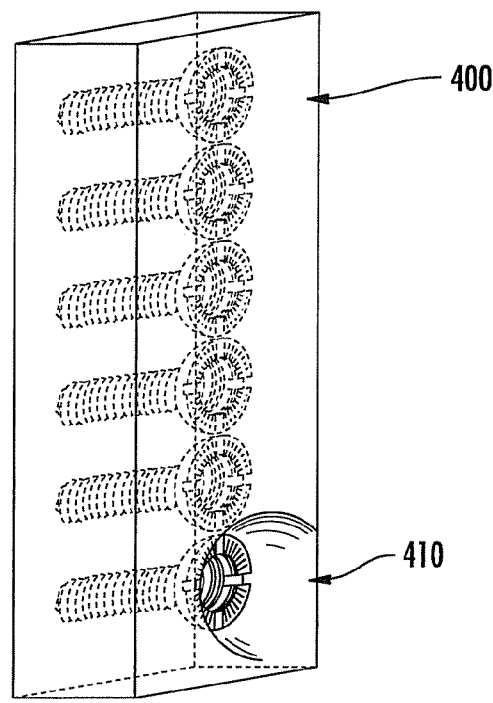
FIG. 7 is a perspective view of a holder adapted to hold screws for use with a screw holder and screwdriver assembly according to an embodiment of the presently disclosed subject matter.

Similarly, in industrial applications where similar length screws are inserted repeatedly, as shown in FIG. 7, a holder 400 (e.g., a clip/cartridge) can be used to hold multiple pins or screws (e.g., pin 101, or any of the embodiments of screw 102), which can be fed (e.g., by spring or gravity) into position behind an opening 410 (e.g., a cone-shaped guide). Use of holder 400 can allow the operator to slide a screwdriver assembly (e.g., first or second screwdriver assembly 201 or 202) into opening 410 and onto head of one of the pins or screws, operate screwdriver assembly in a forward direction, and pull the pin or screw out of holder 400. This process can be repeated for the sequential driving of multiple pins or screws.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter. For example, although first screwdriver assembly 201 and second screwdriver assembly 202 are discussed as being adapted for use with pin 101 and screw 102, respectively, it should be understood that these or other configurations for a screwdriver assembly according to the presently disclosed subject matter can be adapted for use with any of a variety of fasteners, including but not limited to pin 101 and screw 102. Specifically, for example, first screwdriver assembly 201 can be adapted for use with first screw 102a or any of a variety of other fasteners having one or more of the features disclosed herein above. Similarly in this regard, although a variety of different arrangements for screws and screwdriver assemblies are shown and discussed herein, it should be recognized that further configurations having any combination of the features discussed are covered by the present subject matter.

What is claimed is:

1. A screwdriver assembly comprising:
    a hollow sleeve comprising a longitudinal bore and a first end defining a screw engagement surface; and
    a driving shaft positioned within the longitudinal bore of the hollow sleeve and rotatable relative to the hollow sleeve, the driving shaft comprising:
        a first end extending beyond the first end of the hollow sleeve, the first end comprising a protruding tip adapted for engaging a corresponding socket in a head of a screw;
        a second end opposite the first end; and
        a stop with a substantially planar surface restricting axial movement of the sleeve towards the second end of the driving shaft.

2. The screwdriver assembly of claim 1, wherein the protruding tip extends beyond the first end of the hollow sleeve by a distance that is less than a depth of a corresponding socket on the screw.

3. The screwdriver assembly of claim 1, wherein the protruding tip comprises an externally-threaded outer surface adapted for engaging a corresponding threaded socket on the screw.

4. The screwdriver assembly of claim 1, wherein the screw engagement surface comprises a textured surface adapted to engage a textured surface of the head of the screw.

5. The screwdriver assembly of claim 1, wherein the screw engagement surface comprises one or more blades protruding from the first end and adapted to engage one or more corresponding slots in the head of the screw.

6. The screwdriver assembly of claim 5, wherein the one or more blades comprises two blades protruding from the first end on opposing sides of the protruding tip.

7. The screwdriver assembly of claim 5, wherein the one or more blades comprises four blades arranged in a cruciform pattern.

8. The screwdriver assembly of claim 1, comprising a lock movable to selectively link the hollow sleeve to the driving shaft for common rotation of the sleeve and the driving shaft.

9. A method for driving a screw comprising:
    positioning a driving shaft within a longitudinal bore of a hollow sleeve, the driving shaft rotatable relative to the hollow sleeve;
    connecting a screw to the driving shaft by engaging a protruding tip of the driving shaft with a corresponding socket in a head of the screw, wherein when the protruding tip is at least partially engaged with the socket of the screw, a first end of the hollow sleeve contacts the head of the screw;

connecting the driving shaft to a drill to rotate one or both of the driving shaft or the hollow sleeve in a first direction to advance the screw; and rotating the driving shaft in a second direction opposite the first direction to disengage the protruding tip from the socket of the screw.

10. The method of claim 9, wherein connecting a screw to the driving shaft comprises engaging an externally-threaded surface of the protruding tip with a corresponding threaded surface of the socket.

11. The method of claim 9, wherein rotating the driving shaft in the second direction to disengage the protruding tip from the socket of the screw comprises preventing rotation of the hollow sleeve to prevent reverse rotation of the screw.

12. The method of claim 9, comprising engaging the first end of the hollow sleeve with the head of the screw once the protruding tip is at least partially engaged with the socket of the screw.

13. The method of claim 12, wherein engaging the first end of the hollow sleeve with the head of the screw comprises engaging a textured surface of the first end of the hollow sleeve with a textured surface of the head of the screw.

14. The method of claim 12, wherein engaging the first end of the hollow sleeve with the head of the screw further comprises engaging one or more blades protruding from the first end of the hollow sleeve with one or more corresponding slots in the head of the screw.

15. A fixation system comprising:
a screw comprising a threaded screw body and a screw head, the screw head comprising a socket and a screw head surface surrounding the socket; and
a screwdriver comprising:
a hollow sleeve comprising a longitudinal bore and a first end defining a screw engagement surface; and
a driving shaft positioned within the longitudinal bore of the hollow sleeve and rotatable relative to the hollow sleeve, the driving shaft comprising:
a first end extending beyond the first end of the hollow sleeve, the first end comprising a protruding tip adapted for engaging the socket of the screw head;
a second end opposite the first end; and
a stop with a substantially planar surface restricting axial movement of the sleeve towards the second end of the driving shaft.

16. The fixation system of claim 15 wherein the screw head surface comprises a textured surface; and
wherein the screw engagement surface comprises a textured surface adapted to engage the textured surface of the screw head.

17. The fixation system of claim 15, wherein the screw head surface comprises one or more slots; and
wherein the screw engagement surface comprises one or more blades protruding from the first end and adapted to engage the one or more slots.

18. A screw comprising a threaded screw body adapted for engagement of a material and a screw head, the screw head comprising an internally-threaded socket adapted for engaging an externally-threaded driving shaft of a screwdriver and a textured surface adapted to engage a textured surface of the screwdriver.

19. The screw of claim 18, wherein the screw head comprises one or more slots in the surface of the screw head adapted to engage one or more corresponding blades in the screwdriver.

20. A screwdriver assembly comprising:
a hollow sleeve comprising a longitudinal bore and a first end defining a textured screw engagement surface adapted for engaging a textured surface of a head of a screw; and
a driving shaft positioned within the longitudinal bore of the hollow sleeve and rotatable relative to the hollow sleeve, the driving shaft comprising:
a first end extending beyond the first end of the hollow sleeve, the first end comprising a protruding tip adapted for engaging a corresponding socket in the head of the screw;
a second end opposite the first end; and
a stop restricting axial movement of the sleeve towards the second end of the driving shaft.

21. A screwdriver assembly comprising:
a hollow sleeve comprising a longitudinal bore and a first end defining a screw engagement surface;
a driving shaft positioned within the longitudinal bore of the hollow sleeve and rotatable relative to the hollow sleeve, the driving shaft comprising:
a first end extending beyond the first end of the hollow sleeve, the first end comprising a protruding tip adapted for engaging a corresponding socket in a head of a screw,
a second end opposite the first end, and
a stop restricting axial movement of the sleeve towards the second end of the driving shaft; and
a lock movable to selectively link the hollow sleeve to the driving shaft for common rotation of the sleeve and the driving shaft.

22. A method for driving a screw comprising:
positioning a driving shaft within a longitudinal bore of a hollow sleeve, the driving shaft rotatable relative to the hollow sleeve;
connecting a screw to the driving shaft by engaging a protruding tip of the driving shaft with a corresponding socket in a head of the screw, wherein when the protruding tip is at least partially engaged with the socket of the screw, a first end of the hollow sleeve contacts the head of the screw, such that a textured surface of the first end of the hollow sleeve engages with a textured surface of the head of the screw;
rotating one or both of the driving shaft or the hollow sleeve in a first direction to advance the screw; and
rotating the driving shaft in a second direction opposite the first direction to disengage the protruding tip from the socket of the screw.

23. A fixation system comprising:
a screw comprising a threaded screw body and a screw head, the screw head comprising a socket and a textured screw head surface surrounding the socket; and
a screwdriver comprising:
a hollow sleeve comprising a longitudinal bore and a first end defining a screw engagement surface that includes a textured surface adapted to engage the textured surface of the screw head; and
a driving shaft positioned within the longitudinal bore of the hollow sleeve and rotatable relative to the hollow sleeve, the driving shaft comprising:
a first end extending beyond the first end of the hollow sleeve, the first end comprising a protruding tip adapted for engaging the socket of the screw head;
a second end opposite the first end; and
a stop restricting axial movement of the sleeve towards the second end of the driving shaft.

* * * * *